US00PP21991P2

(12) United States Plant Patent
Rutten

(10) Patent No.: US PP21,991 P2
(45) Date of Patent: Jun. 28, 2011

(54) ***HYDRANGEA* PLANT NAMED 'WIM RUTTEN'**

(50) Latin Name: *Hydrangea involucrata*
Varietal Denomination: Wim Rutten

(75) Inventor: Cathrien Rutten, Leende (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/660,108

(22) Filed: Feb. 19, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — June Hwu
(74) *Attorney, Agent, or Firm* — C. A. Whealy

(57) ABSTRACT

A new and distinct cultivar of *Hydrangea* plant named 'Wim Rutten', characterized by its upright, outwardly spreading and mounded plant habit; strong and vigorous growth habit; relatively large leaves; freely flowering habit; and large lacecap-type inflorescences with light violet blue-colored fertile flowers and white-colored sterile flowers.

2 Drawing Sheets

Botanical designation: *Hydrangea involucrata.*
Cultivar denomination: 'WIM RUTTEN'.

BACKGROUND OF THE INVENTION

The present invention relates to a new and distinct cultivar of *Hydrangea* plant, botanically known as *Hydrangea involucrata* and hereinafter referred to by the name 'Wim Rutten'.

The new *Hydrangea* plant is a product of a planned breeding program conducted by the Inventor in Leende, The Netherlands. The objective of the breeding program was to develop strong and vigorous *Hydrangea* plants with attractive leaf and flower coloration.

The new *Hydrangea* plant originated from a cross-pollination in 2000 of two unnamed seedling selections of *Hydrangea involucrata*, not patented. The new *Hydrangea* plant was discovered and selected in 2002 as a flowering plant within the progeny of the stated cross-pollination in a controlled environment in Leende, The Netherlands.

Asexual reproduction of the new cultivar by softwood cuttings in Leende, The Netherlands since 2003 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Wim Rutten'. These characteristics in combination distinguish 'Wim Rutten' as a new and distinct cultivar of *Hydrangea:*

1. Upright, outwardly spreading and mounded plant habit.
2. Strong and vigorous growth habit.
3. Relatively large leaves.
4. Freely flowering habit.
5. Large lacecap-type inflorescences with light violet blue-colored fertile flowers and white-colored sterile flowers.

Plants of the new *Hydrangea* differ primarily from plants of the parent selections in the following characteristics:

1. Plants of the new *Hydrangea* are stronger and more vigorous than plants of the parent selections.
2. Plants of the new *Hydrangea* have larger leaves than plants of the parent selections.
3. Plants of the new *Hydrangea* have larger inflorescences than plants of the parent selections.

Plants of the new *Hydrangea* can be compared to plants of an unnamed selection of *Hydrangea involucrata*, not patented. Plants of the new *Hydrangea* differ primarily from plants of the unnamed selection in the following characteristics:

1. Plants of the new *Hydrangea* are stronger, more vigorous and grow faster than plants of the unnamed selection.
2. Plants of the new *Hydrangea* are shorter and broader than plants of the unnamed selection.
3. Plants of the new *Hydrangea* have longer leaves than plants of the unnamed selection.
4. Plants of the new *Hydrangea* are more freely flowering than plants of the unnamed selection.
5. Plants of the new *Hydrangea* have larger inflorescences than plants of the unnamed selection.

BRIEF DESCRIPTION OF THE PHOTOGRAPHS

The accompanying colored photographs illustrate the unique appearance of the new *Hydrangea* plant, showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a close-up view of a typical flowering plant of 'Wim Rutten' grown in an outdoor nursery.

The photograph on the second sheet is a close-up view of a typical inflorescence and leaves of 'Wim Rutten'.

DETAILED BOTANICAL DESCRIPTION

Plants used in the aforementioned photographs and in the following description were grown during the spring and summer in Grand Haven, Mich. in an outdoor nursery and under conditions which closely approximate commercial production conditions. Plants of the new *Hydrangea* were three years old when the photographs and description were taken. In the following description, color references are made to The Royal Horticultural Society Colour Chart, 1995 Edition, except where general terms of ordinary dictionary significance are used.

Botanical description: *Hydrangea involucrata* 'Wim Rutten'.

Parentage:

*Female, or seed, parent.*—Unnamed seedling selection of *Hydrangea involucrata*, not patented.

*Male, or pollen, parent.*—Unnamed seedling selection of *Hydrangea involucrata*, not patented.

Propagation:

*Type cutting.*—By softwood cuttings.

*Time to initiate roots.*—About three weeks.

*Time to produce a rooted young plant.*—About two months.

*Root description.*—Medium in thickness; creamy white in color.

*Rooting habit.*—Freely branching; dense.

Plant description:

*Form/growth habit.*—Perennial shrub; upright, outwardly spreading and mounded plant habit; broadly inverted triangle; freely branching habit with numerous lateral branches developing per plant; strong and vigorous growth habit; rapid growth rate.

*Plant height.*—About 40 cm.

*Plant diameter or area of spread.*—About 70 cm.

*Lateral branches.*—Internode length: About 9 cm. Texture: Pubescent. Strength: Strong. Angle: About 20° to 30° from vertical. Color, developing: Close to 136B. Color, mature: Close to 197A.

Foliage description:

*Arrangement.*—Opposite, simple.

*Length.*—About 25 cm.

*Width.*—About 7.5 cm.

*Shape.*—Ovate.

*Apex.*—Acute.

*Base.*—Attenuate to cuneate.

*Margin.*—Doubly serrate.

*Texture, upper and lower surfaces.*—Pubescent; rugose.

*Venation pattern.*—Pinnate.

*Color.*—Developing leaves, upper surface: Close to 146A. Developing leaves, lower surface: Close to 146B. Fully developed leaves, upper surface: Close to 138A; venation, close to 138B. Fully developed leaves, lower surface: Close to 138B; venation, close to 138B.

*Petiole.*—Length: About 3.5 cm. Diameter: About 5 mm. Texture, upper and lower surfaces: Pubescent. Color, upper and lower surfaces: Close to 136B to 136C.

Flower description:

*Flower type and habit.*—Single sterile and fertile flowers arranged on terminal lacecap-type panicles; fertile and sterile flowers face upright to outwardly.

*Fragrance.*—Faint, pleasant.

*Natural flowering season.*—Flowering continuous from July to September in Grand Haven, Mich.

*Flower longevity, fertile flowers.*—Flowers last about three weeks on the plant; flowers not persistent.

*Flower longevity, sterile flowers.*—Flowers last throughout the flowering season; flowers persistent.

*Quantity of flowers.*—Freely flowering; about 500 fertile flowers and about 18 sterile flowers per panicle.

*Panicle height.*—About 10 cm.

*Panicle diameter.*—About 17 cm.

*Inflorescence buds.*—Length: About 2.2 cm. Diameter: About 2.2 cm. Shape: Globose. Color: Close to 138C.

*Flower diameter, fertile flowers.*—About 4 mm.

*Flower height, fertile flowers.*—About 3 mm.

*Flower diameter, sterile flowers.*—About 2.8 cm.

*Flower height, sterile flowers.*—About 6 mm.

*Petals, fertile flowers only.*—Quantity/arrangement: Five in a single whorl; star-shaped. Length: About 4 mm. Width: About 2 mm. Shape: Roughly ovate. Apex: Acute. Base: Attenuate. Margin: Entire. Texture, upper and lower surfaces: Smooth, glabrous. Color: When opening, upper and lower surfaces: Close to 96D. Fully opened, upper and lower surfaces: Close to 96D.

*Sepals, fertile flowers.*—None observed.

*Sepals, sterile flowers.*—Quantity/arrangement: Four in a single whorl; cruciform. Length: About 1.5 cm. Width: About 1.3 cm. Shape: Broadly obovate. Apex: Obtuse. Base: Obtuse. Margin: Entire. Texture, upper and lower surfaces: Smooth, glabrous. Color: When opening, upper and lower surfaces: Close to 155A. Fully opened, upper and lower surfaces: Close to 155A.

*Peduncles, fertile and sterile flowers.*—Angle: Mostly erect. Strength: Strong. Length: About 3 cm to 4 cm. Diameter: About 6 mm. Texture: Tomentose. Color: Close to 138C to 138D.

*Pedicels, fertile flowers.*—Angle: About 45° to 80° from vertical. Strength: Strong. Length: About 1 cm. Diameter: About 3 mm to 4 mm. Texture: Tomentose. Color: Close to 138C to 138D.

*Pedicels, sterile flowers.*—Angle: About 30° from vertical. Strength: Moderately strong. Length: About 1.5 cm. Diameter: About 1 mm. Texture: Smooth, glabrous. Color: Close to 155A.

*Reproductive organs, fertile flowers only.*—Stamens: Quantity per flower: About ten. Anther length: About 0.5 mm. Anther shape: Rounded. Pollen amount: Scarce. Pistils: Pistil quantity per flower: Two. Pistil length: About 2 mm. Stigma shape: Oblong. Stigma color: Close to 155A. Style length: About 1.8 mm. Style color: Close to 155A. Ovary color: Close to 145B.

*Seeds/fruits.*—Seed and fruit development have not been observed on plants of the new *Hydrangea*.

Disease/pest resistance: Plants of the new *Hydrangea* have not been observed to be resistant to pathogens and pests common to *Hydrangea*.

Temperature tolerance: Plants of the new *Hydrangea* have been shown to be tolerant to temperatures ranging from about −23° C. to about 37° C.

It is claimed:

1. A new and distinct *Hydrangea* plant named 'Wim Rutten' as illustrated and described.

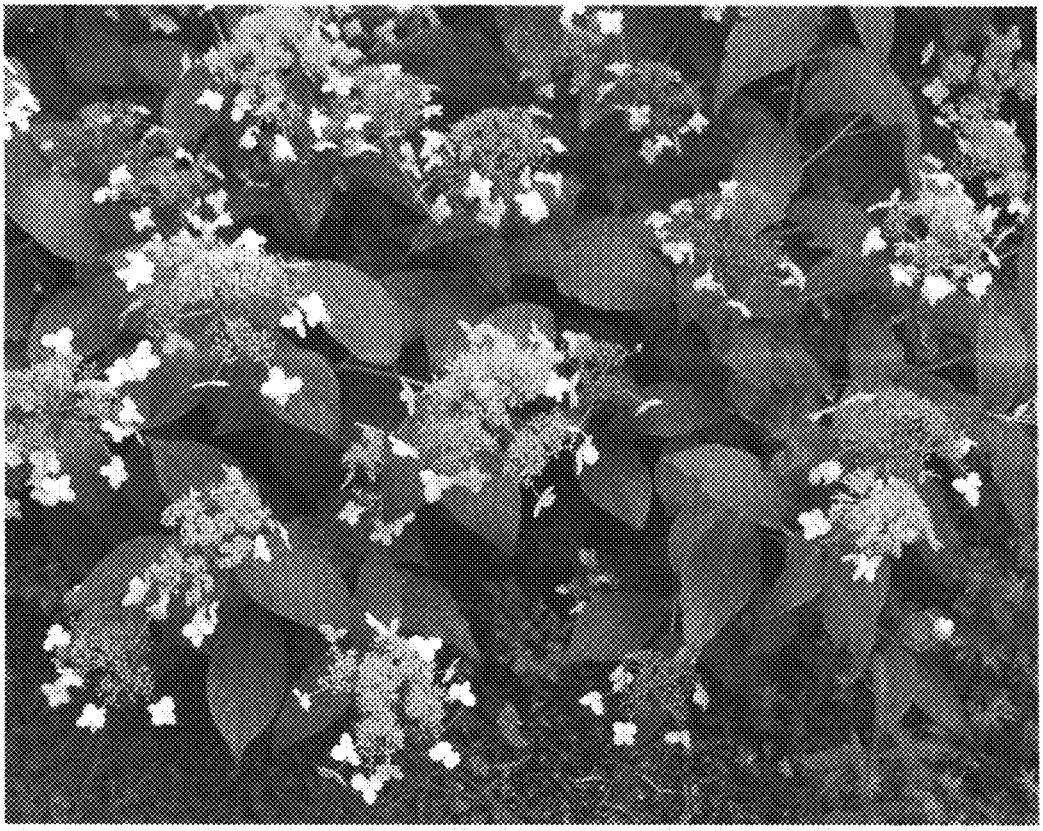

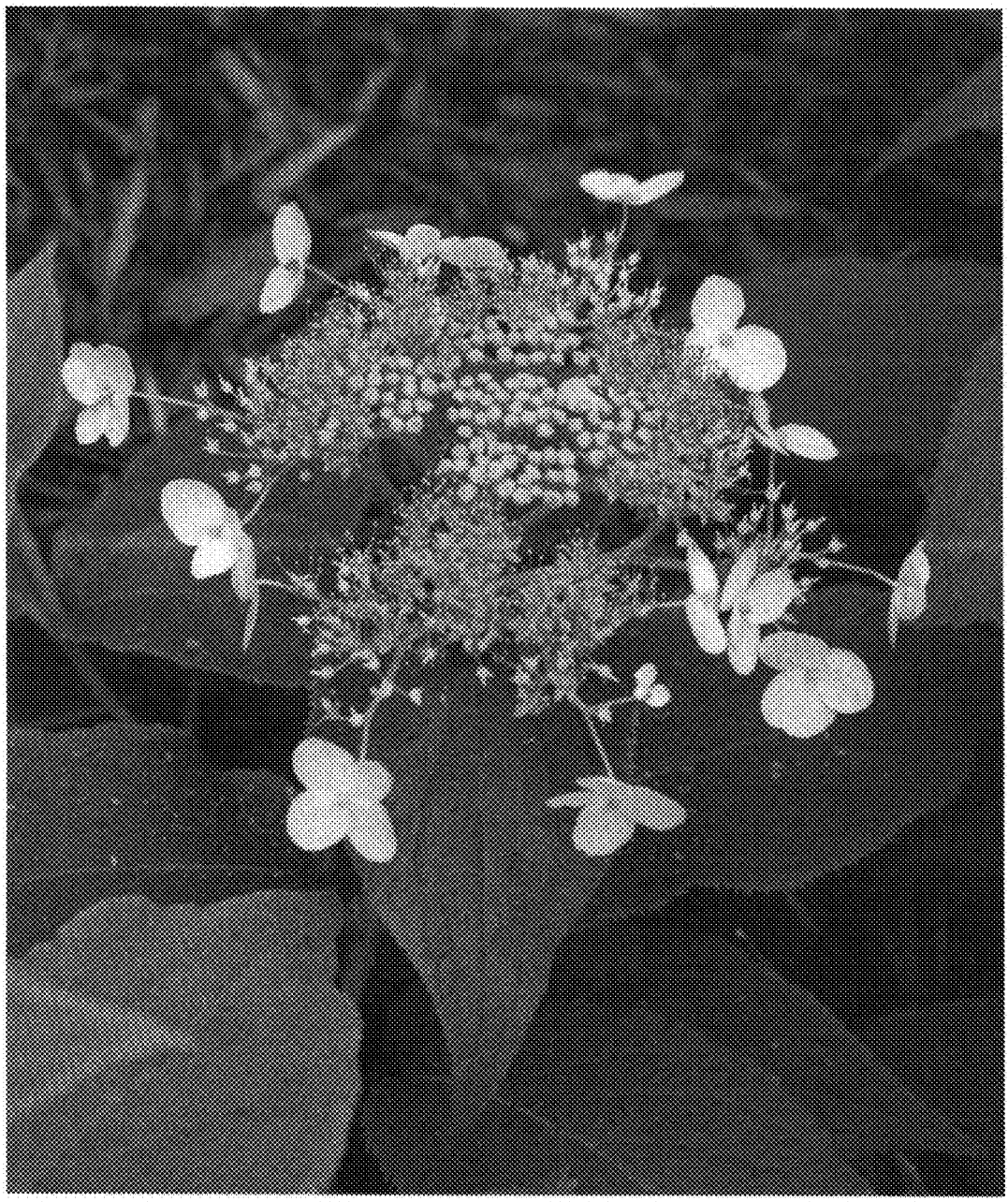

* * * * *